US010401333B2

(12) United States Patent
Boeker

(10) Patent No.: US 10,401,333 B2
(45) Date of Patent: Sep. 3, 2019

(54) FLOW-FIELD-INDUCED TEMPERATURE GRADIENT GAS CHROMATOGRAPHY

(71) Applicant: Peter Boeker, Bonn (DE)

(72) Inventor: Peter Boeker, Bonn (DE)

( * ) Notice: Subject to any disclaimer, the term of this patent is extended or adjusted under 35 U.S.C. 154(b) by 106 days.

(21) Appl. No.: 15/128,993

(22) PCT Filed: Mar. 23, 2015

(86) PCT No.: PCT/DE2015/000131
§ 371 (c)(1),
(2) Date: Sep. 26, 2016

(87) PCT Pub. No.: WO2015/144117
PCT Pub. Date: Oct. 1, 2015

(65) Prior Publication Data

US 2017/0234840 A1 Aug. 17, 2017

(30) Foreign Application Priority Data

Mar. 26, 2014 (DE) ........................ 10 2014 004 286

(51) Int. Cl.
*G01N 30/30* (2006.01)
*G01N 30/54* (2006.01)
*G01N 30/60* (2006.01)

(52) U.S. Cl.
CPC ............ *G01N 30/30* (2013.01); *G01N 30/54* (2013.01); *G01N 30/6047* (2013.01);
(Continued)

(58) Field of Classification Search
CPC ................. G01N 30/461; G01N 30/30; G01N 2030/025; G01N 30/88; G01N 30/12;
(Continued)

(56) References Cited

U.S. PATENT DOCUMENTS 3,146,616 A 9/1964 Loyd
RE30,085 E * 8/1979 Perret ...................... F16J 15/26 62/612

(Continued)

FOREIGN PATENT DOCUMENTS

| | | |
|---|---|---|
| EP | 0 375 410 | 6/1990 |
| GB | 1 355 893 | 10/1972 |
| WO | 97/14957 | 4/1997 |

OTHER PUBLICATIONS

Jesse A. Contreras et al., "Peak Sweeping . . . gas chromatography", Journal of Chromatography, 1278 (2013), 160-165.

(Continued)

*Primary Examiner* — John Fitzgerald
*Assistant Examiner* — Truong D Phan
(74) *Attorney, Agent, or Firm* — Clark & Brody

(57) ABSTRACT

The invention relates to a method, to a device, and to the use of a method for the gas-chromatic separation and determination of volatile substances in a carrier gas by means of a chromatographic separating capillary (1), wherein the separating capillary and/or an enveloping capillary (2) surrounding the separating capillary (1) is electrically conductive and is heated with current in the form of a resistance heater and is cooled by a forced convective flow by means of a fluid in the form of a gradient flow field in such a way that a continuous temperature gradient arises over the length of the separating capillary.

5 Claims, 8 Drawing Sheets

9
6
7
10
11
4
1,2
3
12
15
13
10'
11'
5
8
12'
14

(52) U.S. Cl.
CPC ................ *G01N 2030/3015* (2013.01); *G01N 2030/3023* (2013.01); *G01N 2030/3061* (2013.01)

(58) Field of Classification Search
CPC ........ G01N 30/24; G01N 30/20; G01N 30/32; G01N 2030/324; B01J 2220/54; B01J 20/32; B01D 15/08; B01D 53/0454; H05B 6/62; E21B 43/2401; E21B 43/34; F24H 1/225
USPC ...................... 73/23.39, 23.35, 23.41, 23.42; 210/198.2; 219/772; 95/87, 82, 18
See application file for complete search history.

(56) References Cited

U.S. PATENT DOCUMENTS

| | | | | | |
|---|---|---|---|---|---|
| 4,708,782 | A * | 11/1987 | Andresen | G01N 27/44756 | 204/600 |
| 5,027,643 | A * | 7/1991 | Jenkins | G01N 1/2258 | 422/89 |
| 5,028,243 | A * | 7/1991 | Rubey | G01N 30/30 | 95/87 |
| 5,114,439 | A | 5/1992 | Yost et al. | | |
| 5,135,549 | A | 8/1992 | Phillips et al. | | |
| 5,215,556 | A | 6/1993 | Hiller et al. | | |
| 5,542,286 | A * | 8/1996 | Wang | G01N 30/32 | 73/1.34 |
| 5,733,355 | A * | 3/1998 | Hibino | A01K 1/0152 | 435/262 |
| 5,808,178 | A * | 9/1998 | Rounbehler | G01N 30/30 | 73/23.35 |
| 5,929,321 | A | 7/1999 | Bertrand | | |
| 7,914,612 | B2 | 3/2011 | Rubey et al. | | |
| 2003/0085348 | A1* | 5/2003 | Megerle | G01N 1/2202 | 250/287 |
| 2004/0020855 | A1* | 2/2004 | Allington | B01D 15/206 | 210/656 |
| 2004/0240999 | A1* | 12/2004 | Kamoshita | F04D 29/281 | 416/179 |
| 2007/0029477 | A1* | 2/2007 | Miller | G01N 27/624 | 250/290 |
| 2012/0085148 | A1* | 4/2012 | Amirav | G01N 30/30 | 73/23.39 |
| 2017/0082583 | A1* | 3/2017 | Tarafder | G01N 30/30 | |

OTHER PUBLICATIONS

Coudert, M. et al., “Retention in gas . . . growth rate”, Journal gas of Chromatography A54 (1), p. 1-8, 1971.
Jesse A. Contreras et al., “Dynamic thermal gradient chromatography”, Journal of Chromatography, vol. 1302, p. 143-151 (Jun. 14, 2013).
Phillipps, “On-column temperature . . . along the capillary column”, Jounral of Chromatographic Science 33 (10), p. 541-550, 1995.
P. Boeker et al., “Flow Field Thermal Gradient Gas Chromatography”, Analytical Chemistry, Aug. 14, 2015, pp. 9033-9041.
P. Boeker, “Beginner’s Luck and Hyper-Fast GC”, Analytical Scientist, Issue #0916, Sep. 2016.
P. Sandra, “Go With the Flow (Field)”, the Analytical Scientist, No. 34, Nov. 2015.

* cited by examiner

FLOW-FIELD-INDUCED TEMPERATURE GRADIENT GAS CHROMATOGRAPHY

FIELD OF THE INVENTION

The invention relates to a method and a device for the gas-chromatic separation and determination of volatile substances in a carrier gas by means of a chromatographic separation capillary, wherein the separation capillary and/or a sheath capillary surrounding the separation capillary is/are electrically conductive and is/are heated with current in the form of resistance heating and is/are cooled by a forced convective flow by means of a fluid.

BACKGROUND ART

Nowadays, the method of gas chromatography (GC) is carried out at constant temperatures in the form of isothermal GC or with an increase in temperature during the passage of the substances to be separated through the chromatography column in the form of temperature-programmed GC. In GC laboratory systems, the chromatography column is heated uniformly in an oven chamber with temperature gradients as small as possible (air bath oven). The air bath enables the column to be heated rapidly, with temperature increases of up to 100° C./min being possible in commercial systems.

GC is based on the partitioning equilibrium between the mobile phase, i.e. the carrier gas, and the stationary phase, which is in the form of a thin film on the capillary wall in the case of capillary columns. The rate of transport of substances in the column depends only slightly on speed, i.e. the flow of the mobile phase. It is, in particular, the temperature-dependent phase equilibrium of the substances between the stationary and the mobile phase which determines the rate of transport. In isothermal GC, substances are separated only in a narrow phase equilibrium range. The signals from slowly transported substances at excessively low temperatures are very wide due to the long transport times and the diffusion which occurs in the process. Some substances are not transported and remain at the inlet, head, front part of the separation column. Temperature-programmed GC (TPGC) is carried out in such a way that a temperature level at which transport through the column is achieved is established for all the substances.

Given appropriate matching of the carrier gas speed and of the heating rate of the separation column, good separation is achieved over a wide phase equilibrium range. One disadvantage of this method is that the substances are still being transported in the column during heating and are therefore exposed to higher temperatures than those required for substance separation and transport. This effect is particularly relevant in the case of rapid GC separation processes, in which high heating rates are employed. Raising the temperature too quickly leads to a simultaneous reduction in separation efficiency since the substances are exposed to temperatures favorable for separation only within small time windows and hence within short column sections. After this, it is only transportation that occurs in the remaining section of the separation column since the temperatures are then too high for separation processes.

Gas chromatography with a temperature gradient (TGGC) along the separation column is based on an idea from the Russian scientist Zhukhovitskii. If each substance has a temperature that is characteristic thereof, above which transport takes place at a significant speed (often referred to as the running temperature), a gradient from the inlet (high temperature) to the outlet (low temperature) as the mixture of substances flows in has the effect that each of the substances accumulates at the temperature (and hence location) at which said temperature once again falls below the running temperature. In the first phase of TGGC, the separation column acts as a collecting or enrichment system. If the temperature level is then raised with the gradient being maintained, each substance migrates spatially to the outlet since the running temperature shifts progressively in this direction. If the temperature at the outlet is precisely equal to the running temperature, the substance elutes from the column and is passed to the detector.

The difference with respect to TPGC is that each substance is only exposed precisely to the temperature corresponding to its running temperature and is not merely transported onward into high temperature zones. The temperature at which a substance elutes at the outlet of the separation column is therefore systematically lower in TGGC than in TPGC.

Moreover, a central effect and advantage of TGGC is the focusing effect. Since there is a temperature gradient around each substance, substance fractions which have moved somewhat ahead of the main zone are held back by the lower temperature level prevailing there. However, the fractions which are further back are transported more quickly by the somewhat higher temperature. The effect of extended diffusion (longitudinal diffusion) during transportation in the capillary is thus compensated. By virtue of the narrowness of the substance signals, their height is increased, and hence measurement sensitivity and the signal/noise ratio are improved.

Despite the theoretical advantages of TGGC, the concept has not found broader commercial application. Originally, Zhukhovitskii's idea was implemented in short packed separation columns, around which was arranged a mobile oven segment that was moved mechanically from the inlet to the outlet of the separation columns and produced the gradient within the oven section. In some cases, the separation column or separation capillary was of circular design and the oven was moved around in a circle. The original temperature gradient method with a moving oven on packed columns is also referred to as chromathermography. The emerging process of capillary gas chromatography using thin fused silica separation columns or fused silica separation capillaries had proven highly efficient, even in the case of isothermal and, especially, temperature-programmed applications. The central focus of technical development was to optimize air bath gas chromatographs in respect of heating rates and uniformity of temperature. From a technical viewpoint too, transferring the concept of chromathermography from short rigid packed columns to thin and flexible separation capillaries with a length of many meters had to be regarded as difficult to implement. A number of solutions are known in the prior art for managing the problems associated with chromathermographic methods.

Thus, U.S. Pat. No. 3,146,616 describes how, in the chromathermographic method, an electric heating arrangement which supplies the separation column with the respectively required heating power in individual turns of a heating coil is switched progressively in space, replacing a mechanically moved oven.

DE 21 495 08 discloses a simple concentric arrangement of a heating arrangement around the separation column, through which there is a countercurrent flow of a cold fluid, which heats up along its path and thus produces a temperature gradient in the separation column. To release the collected substances, a hot fluid flowing in a co-current is passed into the concentric chamber.

A mechanically complex arrangement for producing a temperature gradient along a 2.2 m long capillary column is furthermore described in U.S. Pat. No. 5,028,243. The column is introduced as a planar structure in the form of a spiral into a fluid channel and its temperature is controlled by a corresponding planar structure comprising a fluid channel and connecting openings and a heating wire extending there. With this arrangement, even very low temperatures (−100° C. is mentioned) can act on the column. Moreover, this publication discloses an arrangement in which a spirally wound heating wire is arranged in a tubular sheath, through the center of which the separation column extends. In addition, a fluid can be passed through the arrangement, e.g. a very cold gas. The desired temperature gradient can be produced by means of a second heating coil with a decreasing coil spacing.

A TGGC apparatus with double-concentric sheathing of the separation capillary is furthermore described in U.S. Pat. No. 5,215,556. A fluid for heat exchange is passed in a co-current relative to the direction of the carrier gas through a first sheath, and a second fluid is passed through the outer sheath in a countercurrent. As a result, a linear temperature gradient is obtained. In this process, the temperature of the separation column or separation capillary is heated directly by the first fluid.

U.S. Pat. No. 5,929,321 describes a chromathermographic arrangement comprising a moving oven. The oven is guided in a precise manner over the separation column and produces the desired local gradients there. The particular aim of the invention is to improve selectivity in conventional gas chromatography processes in the form of a pre-separation.

A double-concentric arrangement comprising a coiled separation column on a holder in a tube is disclosed in U.S. Pat. No. 7,914,612 B2. The arrangement is supposed to be about 10 cm long and encloses a 1 to 5 m long separation column. Once installed in an oven, cold fluid is additionally supplied to produce a temperature gradient.

US 2012/0085148 (A1) discloses an additional system for a conventional gas chromatograph, comprising a looped metal capillary, in which a short conventional fused silica separation column is inserted. The aim of the system development is temperature-programmed gas chromatography with very quick heating and cooling cycles. The application relates to a resistance heater, wherein the gas chromatograph is operated with a resistance heater but without the use of a temperature gradient.

U.S. Pat. No. 5,114,439 likewise describes a coiled arrangement of a resistance-heated capillary column, particularly for mobile uses. The temperature is measured by measuring the resistance, although heating of the separation capillary takes place without a gradient.

In U.S. Pat. No. 5,135,549, four techniques for producing a temperature gradient are presented. There, the use of gradients is generally described in certain configurations, wherein the techniques mentioned describe resistance heating via a coating, in particular a wound heater with a variable winding density of a heating wire, a longitudinally directed coolant flow along a heated capillary with continuous warming up of the coolant and a separation column heated separately to different temperatures.

U.S. Pat. No. 5,808,178 discloses a “flash GC”, wherein a resistance-heated metal sheath capillary, in which the GC column is guided. A cooling trap, through which there is an alternating direction of flow by means of a valve arrangement, is additionally described in this patent. In particular, the problematic influence of temperature differences between the lower and upper capillary turns is mentioned in the description of the patent.

As can be seen from the prior art, implementing a uniform temperature gradient along a capillary column of several meters length is a difficult technical challenge. In particular, the temperature must varied very uniformly, with even short deviations leading to delays in substance transport (if undershot) and hence to distorted signal shapes.

To solve the technical problem, separation capillaries have admittedly also been coated with conductive coatings of decreasing thickness in order to allow differences in temperature adjustment by way of the gradual change in resistance, or the temperature gradient has been produced directly around a metal separation column or separation capillary using a heating wire coil with a continuous increase in winding density. Attempts have also been made to work with a resistance-heated separation column which is sheathed concentrically by a guide tube and in which cold nitrogen is passed in a countercurrent with respect to the carrier gas direction in the guide tube and the heated separation column is cooled more intensely with the still-cold fluid at the outlet than with the already heated fluid at the outlet (cf. PHILLIPS, J. B.; JAIN, V. (1995): On-column temperature programming in gas-chromatography using temperature-gradients along the capillary column. In: JOURNAL OF CHROMATOGRAPHIC SCIENCE 33 (10), pages 541-550; COUDERT, M.; VERGNAUD, J. M. (1971): Retention in gas chromatography obtained with a longitudinal temperature gradient with a constant growth rate. In: JOURNAL OF CHROMATOGRAPHY A 54(1), pages 1-8. DOI: 10.1016/S0021-9673(01)80238-7; Contreras, Jesse A.; Rockwood, Alan L.; Tolley, H. Dennis; Lee, Milton L. (2013): Peak sweeping and gating using thermal gradient gas chromatography. In: JOURNAL OF CHROMATOGRAPHY A 1278, pages 160-165).

Common to all technical solutions hitherto is a high outlay on production. These implementations are not suitable for commercial use. Thus, for TGGC analyses in accordance with the prior art, the separation columns have to be modified manually or mounted laboriously on supports to enable the temperature thereof to be spatially controlled by means of temperature control fluids.

SUMMARY OF THE INVENTION

It is therefore the object of the invention to provide a TGGC in which efficient separation can be achieved with commercially available separation capillaries that can be interchanged easily and do not require any special temperature control fluids but allow dynamic temperature control with a gradient and entail the use of only small amounts of energy for temperature control.

DETAILED DESCRIPTION OF THE INVENTION

Figure 1:
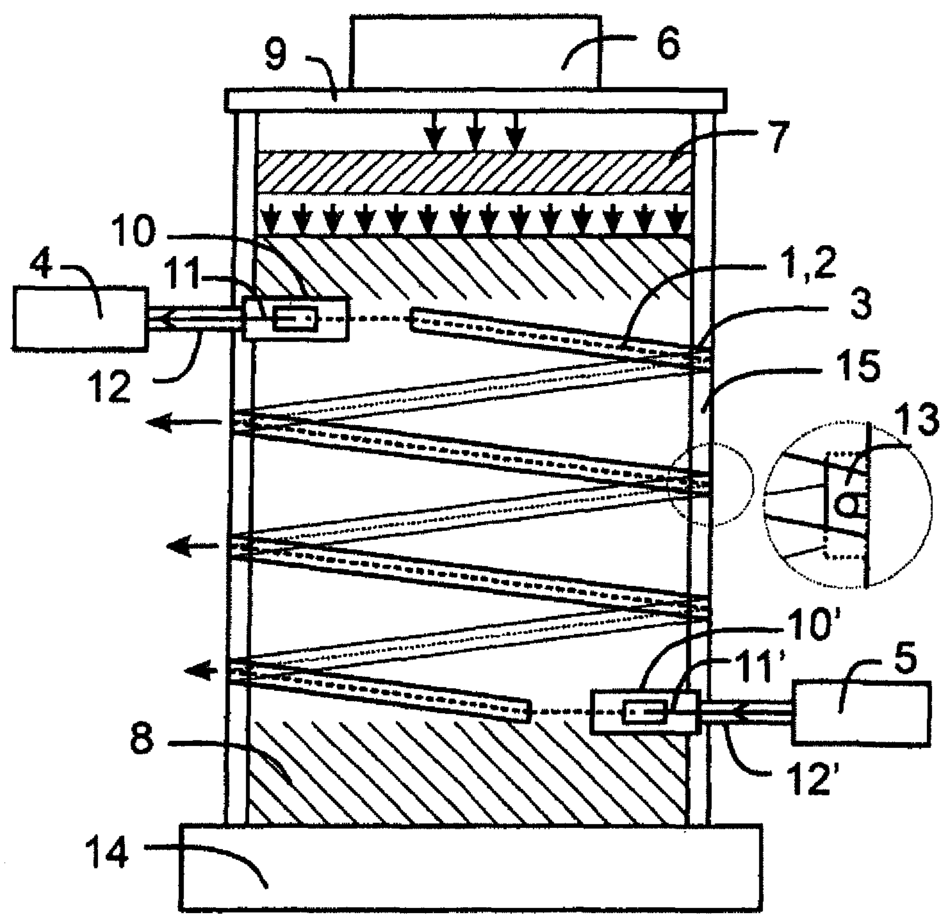
FIG. 1 shows a vertical section through a Gas chromatography with a temperature gradient (TGGC).

The invention is based on a thermal balance equilibrium directly at and in the resistance-heated separation column between heat production by the lost electric power and heat dissipation by a forced flow and heat radiation by the capillary column. The temperature gradient is produced by a gradient flow field. The flow to the separation column is at different speeds of flow across the separation column and, in this way, the temperature drop between the inlet and the outlet of the separation column is produced.

The advantage over the prior art is that there is no need to produce a thermal gradient field around the separation column, which then warms or heats the separation column only indirectly to the desired temperatures.

On the contrary, the temperature gradient arises as a consequence of the gradually changing thermal balance, thus making it possible to construct a precise and rapidly operating gas chromatography system.

According to the invention, an electrically (resistance-) heated separation capillary and/or a sheath capillary surrounding the separation capillary is used instead of an oven, which is used according to the prior art. It is possible to heat both the electrically heated separation capillary in a controlled manner with a rapid temperature program while the substances to be analyzed are carried through by means of a carrier gas and, in the case where a sheath capillary surrounding the separation capillary is used, the actual fused silica separation capillary is guided in such a way in the interior that it can be heated in a controlled manner with a rapid temperature program, while the substances to be analyzed are carried through by means of a carrier gas. According to the invention, the sheath capillary surrounding the separation capillary is produced from a solid body and can comprise a ceramic, e.g. $Si_3N_4$. However, it is also possible for the solid body to be composed of metal, in particular stainless steel. It is furthermore also possible to use nickel, nickel alloys or other metals with a suitable resistance as solid bodies. If an electrically conductive separation capillary is used, the use of a separate sheath capillary is superfluous. As a heating method for the separation columns, use is made of resistance heating since it combines the highest heating rates and high energy efficiency (low thermal masses). In the case of the resistance heating systems used to date in the prior art for temperature-programmed gas chromatography, a thermal equilibrium is established through natural convection and the heat transport thus effected. However, it is disadvantageous here that the level of heat transport in the case of natural convection depends on the orientation of the heated capillary in space. A horizontal capillary is cooled more by natural convection than a vertical capillary, which undergoes less heat transport in the upper part due to rising warm air components. Vertically wound capillary loops therefore exhibit nonuniform temperatures.

Disproportionately greater than heat transport due to natural convection is heat transport due to forced convection. If a heated capillary is subject selectively to a flow the cooling effect and hence the stable equilibrium temperature is heavily dependent on the speed of flow. This opens up the possibility of setting the temperature of a heated capillary within wide limits by selectively varying the incident flow to said capillary. Thus, according to the invention, it is envisaged that the resistance heating of the separation capillary (or of a sheath capillary around the separation column) takes place in a suitable flow field which has a uniform speed of flow gradient along the separation column. For this purpose, a TGGC has a unit for producing air flow, wherein this can be a fan or a blower or, alternatively, a pressurized gas supply with a suitable throttle valve. The fan or blower can be switched on and off by an electronic open-loop and closed-loop control unit. Alternatively, a pressurized gas supply can be switched on and off by means of a solenoid valve, for example. If expanded control capacity is desired for carrying out the TGGC method, the power of the fan or blower can be electronically controlled in order to deliver a variable volume flow. In corresponding fashion, it is also possible for the pressurized gas supply to deliver a variable volume flow using a control valve.

In this case, the TGGC comprises a separation capillary which is mounted in a flow field with a speed gradient. The production of the speed gradient can be accomplished in various ways, for which purpose, in particular, widening of a flow channel, continuous discharge of fractions of the flow and a continuous increase in flow resistance (pressure loss) may be mentioned.

To achieve a continuous temperature field in the form of a gradient, it is possible to use an electronic open-loop and closed-loop control unit. The unit performs open-loop and closed-loop control of the temperature of the separation capillary or the temperature of the sheath capillary surrounding the separation capillary by regulating the applied voltage and hence the power loss produced. The actual value for the open-loop and closed-loop control is supplied by a temperature sensor. This can be a thermocouple with a low thermal mass, which is mounted on the capillary by means of a high temperature adhesive. As an alternative, an infrared optical temperature sensor can be used, said sensor measuring the temperature of the capillary without making contact. The electronic open-loop and closed-loop control unit furthermore regulates fluid flow for controlled production of the flow gradient around the separation capillary. The electronic open-loop and closed-loop control unit has further connections, by means of which external devices, such as sample applicators, thermodesorbers or laboratory robots, can be controlled or control commands can be received from such external devices. After a start command, the electronic open-loop and closed-loop control unit performs a measurement cycle divided into phases.

It is very important to carry out this temperature control homogeneously since otherwise there is disadvantageous retardation of the individual substances. Here, homogeneous is intended to mean that the temperature variation is uniform over the length of the sheath capillary and that no zones with an alternating higher and lower temperature occur.

The thermal balance for the heated separation capillary subject to an incident flow of a fluid and/or for the sheath capillary surrounding the separation capillary can be calculated since there is a well-developed theory for this in the scientific/technical literature. The thermal balance comprises the heat energy supplied, the convective dissipation and the radiated heat energy.

$$Q_{Thermoelectric}=Q_{Convection}+Q_{Radiation}$$

with individual contributions as follows:

$$Q_{Thermoelectric}=U*I=I^2*R=U^2/R$$

$$Q_{Convection}=\alpha_{mean}*A*(T_{Wall}-T_\infty)$$

$$Q_{Radiation}=\sigma_{Boltzmann}*(T_{Wall}^4-T_\infty^4)$$

The most laborious part of the balance is the calculation of the proportion attributable to convection. The heat transport coefficient is calculated using the tools of similarity theory and the dimensionless parameters defined there.

A distinction is drawn between free convection and forced convection. Free convection occurs due to density differences which arise during the heating of a fluid around a body, e.g. the convection of air around a heated separation capillary and/or the sheath capillary surrounding the separation capillary. Forced convection occurs in flows which are driven by way of pressure differences by means of fans or blowers. The flow is much more intense around the heated body and therefore heat dissipation is therefore also greater.

Calculation is performed using the dimensionless Nusselt number. The Nusselt number expresses the relationship between heat transfer and heat conduction in the fluid, this being additionally associated with a characteristic length. The central concept of similarity theory with its dimensionless parameters is to obtain universally valid calculation equations which can be applied to different dimensions or different physical characteristics.

The Nusselt number is defined as:

$$Nu = \frac{\alpha_m * L}{\lambda_{Fluid}}$$

where $\alpha_m$: mean heat transfer coefficient [W/(m$^2$*K)]

$\lambda_{Fluid}$: heat transfer coefficient of the fluid [W/(m*K)]

L: characteristic length, here diameter d [m]

In order to calculate the Nusselt number, the Grashof, Prandtl and Rayleigh numbers are required in the case of free convection. For forced convection, the Reynolds number and the Prandtl number are used. It is typical of this type of calculation that use is made of parameters that establish further physically characteristic relationships. Moreover, the Grashof number expresses a dimensionless relationship between the lift forces due to density differences in the fluid and gravitational acceleration in the case of free convection.

$$Gr = \frac{L^3 * g * \beta_\infty * (T_{Wall} - T_{Fluid})}{\nu_{Fluid}}$$

where:

$\beta\propto$: thermal expansion coefficient at $T_{Fluid}$[1/K]

$$\beta_\infty = \frac{1}{T_{Fluid}}$$

in the case of ideal gases $\nu_m$: kinematic viscosity at $T_m$[m$^2$/s]

g: gravitational acceleration [m/s$^2$]

The Prandtl number links flow variables with heat conduction variables in the fluid.

$$Pr = \frac{\eta_{Fluid} * c_p}{\lambda_{Fluid}}$$

where:

$c_p$: specific isobaric heat capacity [J/(kg*K)]

$\eta_m$: dynamic viscosity at $T_m$[kg/(m*s)]

For temperatures between 0 and 500° C., the Prandtl number for air is between 0.71 and 0.72 and can therefore be assumed to be constant. In the calculation formulae, the Rayleigh number is often used as the product of the Grashof and Prandtl numbers.

$$Ra=Gr*Pr$$

In the case of heat transfer of a horizontal cylinder (capillary) with natural convection, the following calculation relation is given for the Nusselt number:

$$Nu_m = \left\{0.60 + \frac{0.387 * Ra^{1/6}}{[1 + (0.559/Pr)^{9/16}]^{8/27}}\right\}^2$$

Here, the characteristic length is the diameter of the capillary. For forced convection, the following is given for the Nusselt number:

$$Nu_m = c \times Re^m \times Pr^n \left(\frac{Pr}{Pr_0}\right)^p$$

With the factor and the exponents as a function of the Reynolds number[1]:

| Re | c | m | n |
|---|---|---|---|
| 1 to 40 | 0.76 | 0.4 | 0.37 |
| 40 to 1000 | 0.52 | 0.5 | 0.37 |
| 1000 to 2*10$^5$ | 0.26 | 0.6 | 0.37 |
| 2*10$^5$ to 10$^7$ | 0.023 | 0.8 | 0.4 |

Heating of the fluid: p = 0.25
Cooling of the fluid: p = 0.20

[1]Baehr, Hans Dieter; Stephan, Karl (2006): Wärme- und Stoffübertragung [Heat and Substance Transfer], 5$^{th}$, revised edition, Berlin [inter alia]: Springer The Reynolds number is calculated as follows:

$$Re = \frac{w_\infty \times d_{Cylinder}}{\nu_{T_m}}$$

$w_\infty$: speed of flow at a long distance from the cylinder [m/s]

$d_{cylinder}$: characteristic length, here diameter [m]

$\nu_m$: kinematic viscosity at $$T_m[\mathrm{m}^2/\mathrm{s}]$$

In the equation for the Reynolds number, w (infinite) is the speed of flow at a long distance from a cylindrical body, e.g. a heated separation capillary and/or a sheath capillary surrounding the separation capillary, d is the diameter of the cylindrical body (capillary) and $\nu_m$ is the viscosity at the mean temperature.

$Pr_0$ is the Prandtl number at wall temperature. Since the Prandtl number in the case of air is in a range of between 0 and 300° C. at 0.71, the last factor of the equation is approximately equal to 1 and the penultimate factor is constant at $0.7^{037}$ in a wide range of Reynolds numbers. For calculation, the substance values $\lambda_m$ and $\nu_m$ (and possibly also $\eta_m$) must be calculated. With these values, there is a high dependence on temperature. The calculations are therefore designed for use with a mean temperature between the (high) wall temperature and the (lower) fluid temperature at a relatively long distance:

$$T_m = \frac{T_{Wall} + T_\infty}{2}$$

In the range between 0 and 500° C., the following equations obtained by regression using absolute temperature values in the unit Kelvin, Thermal Conductivity:

$$\beta = -6.0054*10^{-4} + 1.0732*10^{-4}*T - 7.0019*10^{-8}*T^2 + 3.2779*10^{-11}*T^3 \text{ [W/(m}^2\text{K]}$$

Kinematic Viscosity:

$$\nu = -1.9058*10^{-6} + 2.17926*10^{-8}*T + 1.36208*10^{-10}*T2 - 3.25327*10^{-14}*T3 \text{ [m}^2\text{/s]}$$

To make the above statements more specific, the following calculations for the temperature variations with forced convection and different speeds of flow are shown:

For comparison, the equilibrium temperatures calculated for natural convection are calculated and also shown for the same heat outputs.

Calculation for forced convection, 1 mm diameter capillary

| Speed of flow v m/s Air at 20° C. | Temperature of the capillary T ° C. for epsilon = 1, P = 51.29 W/m | Differential temperature T ° C. at v = 0.1 m/s | Temperature of the capillary T ° C. for epsilon = 0, P = 33.39 W/m | Differential temperature T ° C. at v = 0.1 m/s |
|---|---|---|---|---|
| 0.1 | 300.0 | | 300.0 | |
| 0.2 | 262.4 | 37.6 | 234.1 | 65.9 |
| 0.3 | 239.5 | 60.5 | 202.8 | 97.2 |
| 0.4 | 223.3 | 76.7 | 183.5 | 116.5 |
| 0.5 | 210.9 | 89.1 | 169.8 | 130.2 |
| 0.6 | 201.0 | 99.0 | 161.7 | 138.3 |
| 0.7 | 192.8 | 107.2 | 151.4 | 148.6 |
| 0.8 | 185.8 | 114.2 | 144.7 | 155.3 |
| 0.9 | 179.8 | 120.2 | 139.1 | 160.9 |
| 1 | 174.5 | 125.5 | 134.3 | 165.7 |
| 2 | 142.5 | 157.5 | 107.0 | 193.0 |
| 3 | 126.2 | 173.8 | 94.2 | 205.8 |
| 4 | 115.7 | 184.3 | 86.2 | 213.8 |
| 5 | 108.2 | 191.8 | 80.6 | 219.4 |

Calculation for natural convection

| Air at 20° C. | for epsilon = 1, P = 51.29 W/m | for epsilon = 0, P = 33.39 W/m |
|---|---|---|
| | 320.0 | 331.1 |

Figure 8:
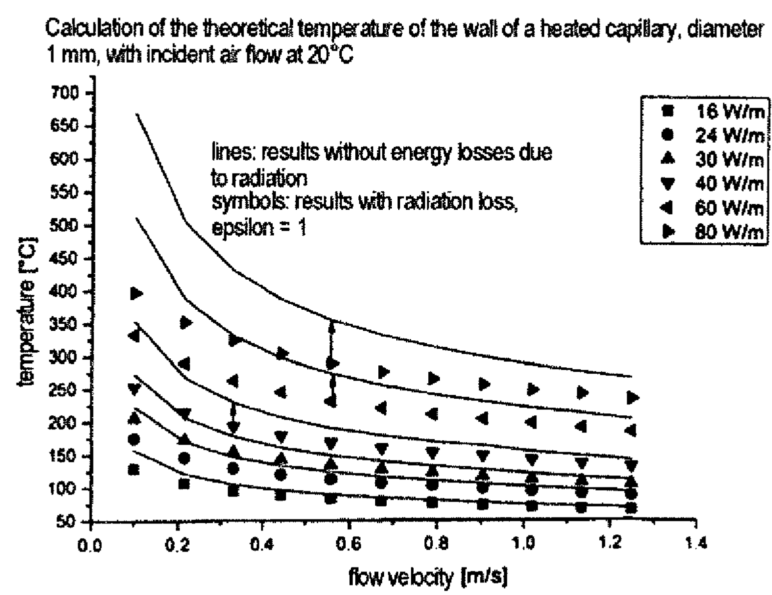
FIG. 8 shows the calculations of the temperatures of the wall of the heated capillary in the case of forced convection with and without a radiation component (epsilon equal to 1 or 0), wherein the heated capillary has a diameter of 1 mm and there is an incident flow of air at 20° C. with variable speeds of flow.

In FIG. 8, there is a depiction of the calculations of the temperatures in the case of forced convection with and without a radiation component (epsilon equal to 1 or 0), wherein the heated capillary has a diameter of 1 mm and there is an incident flow of air at 20° C. with variable speeds of flow.

The gas-chromatographic measurement of volatile substances by means of the method according to the invention and by means of the device according to the invention is described below by way of example:

1. In the initial position, power and temperature control and volume flow control are switched off. However, the temperatures of the transfer lines from the applicator unit and to the detector are controlled (typically in the region of about 200° C.). The transfer ovens for connection of the uncoated transfer lines to the separation capillary are also at the required high temperature (typically 300-350° C.).
2. In response to a control command, temperature control is activated and a lower temperature control value for the separation capillary and/or for the sheath capillary surrounding the separation capillary is/are set. In parallel with this, fluid flow control is set to a fixed fluid flow. A typical lower temperature value in this phase is 40° C. at the outlet of the separation capillary, wherein the outlet should be taken to be the region of transition to the detector.
3. A control command starts measurement with the TGGC. The sample to be analyzed or the volatile substances to be tested are then carried into the separation capillary by a carrier gas, such as helium, hydrogen, nitrogen or air.
4. After injection of the substances to be analyzed, a waiting time to be specified is executed by the electronic open-loop and closed-loop control unit. In this waiting time, solvent fractions from the sample application, for example, can be flushed out of the separation capillary. This waiting time is typically in the region of a few seconds.
5. After this waiting time, the controlled raising of the temperature of the separation capillary and/or of the sheath capillary surrounding the separation capillary begins. Time intervals in the region of a few seconds to the single-digit minute range are targeted. During the raising process, the substances to be analyzed are transported through the separation capillary by means of the carrier gas and by means of the gradient. The setpoint of the temperature control process can be measured at the beginning or at the end of the separation column, depending on the intended chromatographic measurement method. A typical embodiment comprises the ramp-shaped raising of the temperature with a particular rate of rise per time unit, e.g. in the range of from 5 to 60° C./s. Thus the temperature range of 300° C. (e.g. 40° C. to 340° C.) is traversed in between 5 and 60 s. Depending on the substances to be analyzed, the ramp-shaped increase can also be implemented in several stages at different rates of rise. Intermediate holding phases are also possible. During the process of raising the temperature of the separation capillary and/or of the sheath capillary surrounding the separation capillary, the temperature gradient over the length of the separation capillary is produced by the continuous gradient of the flow field. The fluid flow can remain constant during the raising phase but can also be raised or lowered. The level of the fluid flow affects the level of the gradient, i.e. the differential temperature between the inlet and the outlet of the separation capillary, i.e. the locations of injection and detection.
6. After the upper control value for temperature control has been reached, there follows a measurement phase, in which this temperature is regulated to a constant level. At the same time, the fluid flow is adjusted downward or switched off. Owing to the reduction or elimination of the flow gradient around the separation capillary, the temperatures between the inlet and the outlet of the separation capillary balance out. The conditions of natural convection with the associated equilibrium temperatures then prevail there. The electronic temperature control system holds the temperature constant at the actual-value measurement location by controlling the power of the heating current. If the actual-value measurement location is at the outlet of the separation capillary (low temperature during flow), there is a decrease in the inlet temperature to the level of the outlet temperature in this phase. If the actual-value measurement location is at the inlet of the separation capillary, the temperature at the outlet will rise to the level at the inlet. According to the invention, the inlet is taken to be the region where the volatile substances to be analyzed are injected. Raising the outlet temperature means that even substances of low volatility are transported out of the separation capillary.

7. After the end of this measurement phase, the temperature can be held constant in a further phase in order to continue flushing out contaminants.
8. In a final phase, the unit for producing an air flow, e.g. a fan or a blower, is set to maximum values. The heating power for the separation capillary is switched off. There is therefore a very rapid decrease in the temperature to the values required at the beginning of a new measurement process.

The invention is explained once again in greater detail by means of the following figures:

FIG. 1 shows a vertical section through a TGGC. It can be seen that the TGGC is bounded by a base (14), by a cover (9) and by lateral wall surfaces of a hollow cylinder (15). Milled into the wall of the hollow cylinder (15) is a helical groove (3), in which a separation capillary (1) and/or a sheath capillary (2) surrounding the separation capillary (1) can be arranged. If the hollow cylinder (15) has a diameter of 20 cm, for example, the separation capillary (1) and/or the sheath capillary (2) surrounding the separation capillary (1) can have a groove length or separation capillary length of 60 cm per turn. Mounted in the cover (9) is a fan or a blower (6), by means of which a fluid, e.g. air, is blown into the interior of the hollow cylinder (15). To stabilize the flow downstream of the fan or blower (6), a flow stabilizer (7) is fitted. The injected air can escape from the groove (3) and leads to an air flow in the groove (3). In order to reduce this air flow uniformly from the top downward, a porous material (8) is introduced into the hollow cylinder (15) or the TGGC. According to the invention, an open-cell filter foam can be used as a porous material (8), wherein the use, mentioned by way of example, of open-cell filter foam is not intended to represent a restriction to a particular type of material. All other possible materials which allow controllable pressure reduction can be used, e.g. polyurethanes, silicates or aramids. In this way, a uniform and continuous flow variation from the top downward is achieved, in particular in the downward slope of the groove (3). Uncoated transfer lines (11, 11') can furthermore be seen in the region of the sample applicator (5) or of the injection location and in the region of the detector (4), said lines being connected in heated transfer ovens (10, 10') to the separation capillary, via which the volatile substances to be analyzed enter the TGGC and are identified after measurement at the outlet by means of the detector (4). Auxiliary heating arrangements (12, 12') for the transfer lines ensure retardation-free transport of the substances to be analyzed. The separation capillary (1) and/or the sheath capillary (2) surrounding the separation capillary (1) are held at defined angular spacings on the inner walls of the TGGC by a thin-walled holding plate (13), in the center of which there is a guide hole or a guide groove.

The flow is hardly reduced by these very thin holding plates (13), being reduced only directly in the holding plates (13) and in the directly adjoining boundary layer. The absence of flow or the reduced flow leads to an increase in the temperature only in a very small region since the cooling effect of the flow is absent or reduced. This slight local temperature increase is not disruptive for the TGGC since the substances pass through this region quickly and are then once again subject to the gradient profile. A holding plate consisting of a compound with a low thermal conductivity, e.g. high-temperature polymers or ceramics, is preferably selected.

The substances to be analyzed come from a sample feeder (5). The sample feeder (5) can be a gas-chromatographic injector, a thermodesorption unit or some other collecting and application system. The detector (4) is connected to the cold end of the separation capillary (1) via the transfer line (11). Any gas-chromatographic detector, such as FID, ECD, PID, WLD and even mass spectrometers, such as a quadrupole mass spectrometer or TOF mass spectrometer, can be used as a detector (4). Gas sensors or gas sensor arrays can also be operated with the pre-separation in the TGGC.

Figure 2:
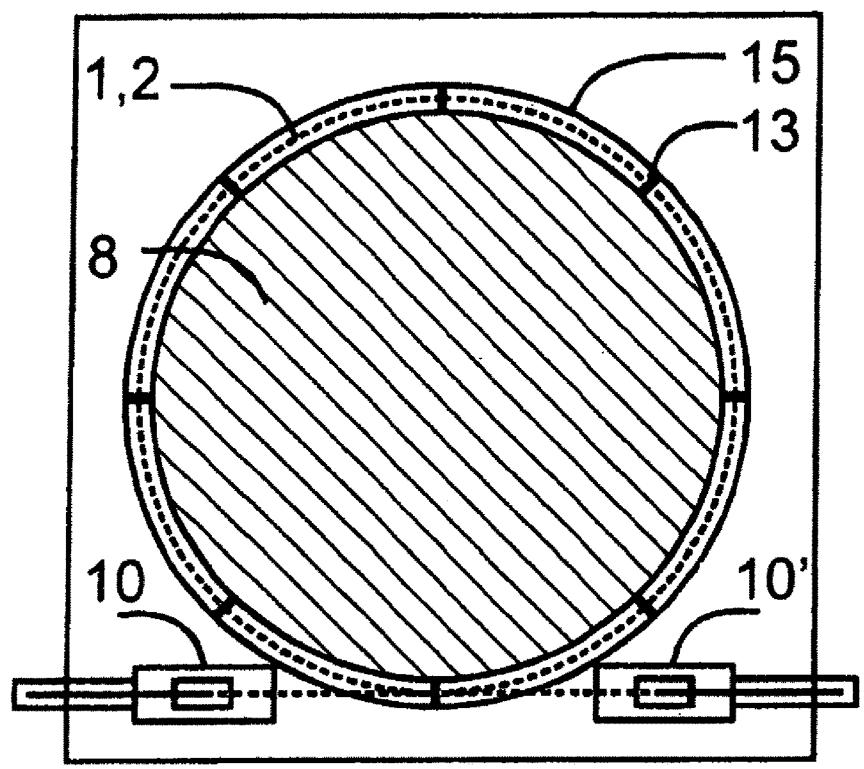
FIG. 2 shows a horizontal section through a TGGC.

FIG. 2 shows a horizontal section through a TGGC. It shows the hollow cylinder (15) into which a separation capillary (1) is inserted by means of a helical groove (3). By means of holding plates (13), which are arranged over the entire circumference of the hollow cylinder (15), the separation capillary (1) is secured in the helical groove (3) of the hollow cylinder (15) of the TGGC. There is porous, pressure-reducing material (8) in the interior of the cylindrically configured TGGC in order to ensure a continuous flow gradient. The transfer ovens (10 and 10') are furthermore situated in the inlet and outlet regions of the separation capillary (1).

Figure 3:
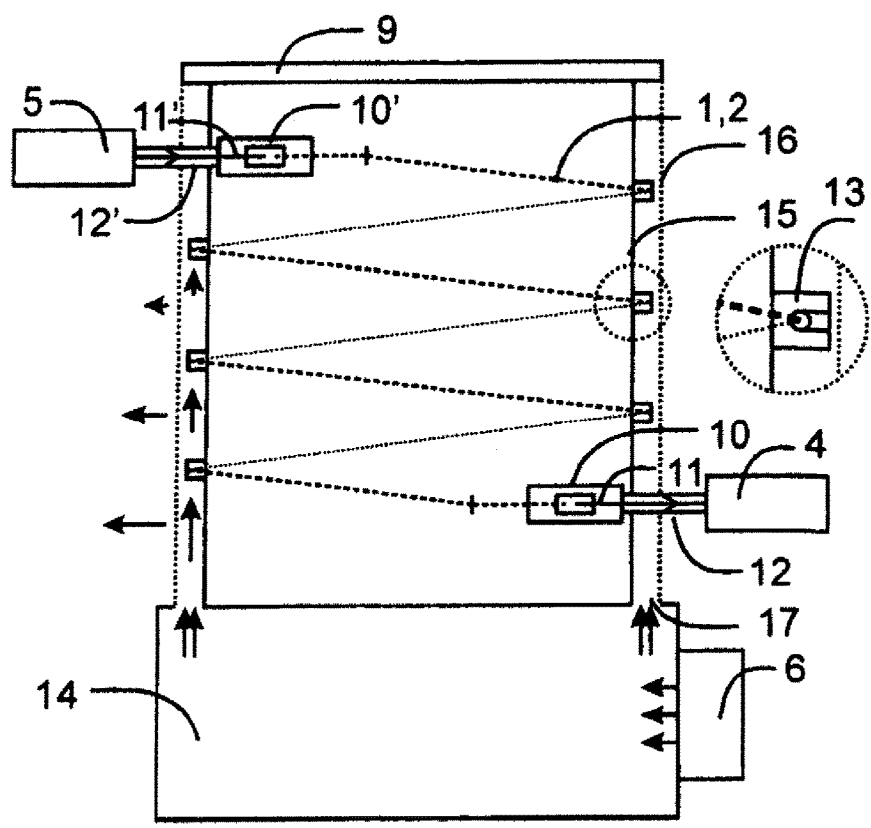
FIG. 3 shows a TGGC with continuous flow discharge via a partially permeable wall surface (16), e.g. a permeable fabric or a wire mesh.

In a vertical section, FIG. 3 shows a TGGC with continuous flow discharge via a partially permeable wall surface (16), e.g. a permeable fabric or a wire mesh. By means of a unit for producing a fluid flow, e.g. a fan or a blower (6), a fluid, e.g. air, is introduced laterally into the base (14) of the TGGC. Via the base (14), the fluid passes via an annular groove (17) in the base (14), into the jacket region between the fixed wall of a hollow cylinder (1) and a wall surface (16) that is partially permeable for the fluid. The separation capillary (1) and/or the sheath capillary (2) surrounding the separation capillary (15) are held at defined angular spacings on the wall of the hollow cylinder (15) of the TGGC by thin-walled holding plates (13), in the center of which there is a guide hole or a guide groove. The separation capillary (1) and/or sheath capillary (2) is/are directed helically from the bottom up in the jacket region between the hollow cylinder (15) and the partially permeable wall surface (16). Some of the fluid is discharged to the environment via the partially permeable wall surface (16) or jacket surface on the path of the flow from the bottom up, with the result that the fluid flow decreases continuously from the bottom up due to the discharge of the fluid. As a result, a flow field with a speed of flow that decreases from the bottom up is established. The thermal balance equilibrium at the heated separation capillary (1) and/or sheath capillary (2) therefore likewise shifts continuously, with the result that the temperature is lower at the bottom where the flow is greater than at the top, where the flow is less. Moreover, the TGGC has transfer ovens (10, 10') in the inlet and outlet regions, in which ovens transfer lines (11, 11') are connected to the separation capillary, and heating and insulation elements (12, 12') to control the temperature of the transfer lines. A sample applicator (5) or injection location can furthermore be seen in the inlet region of the TGGC, and a detector (4) can be seen in the outlet region of the TGGC.

Figure 4:
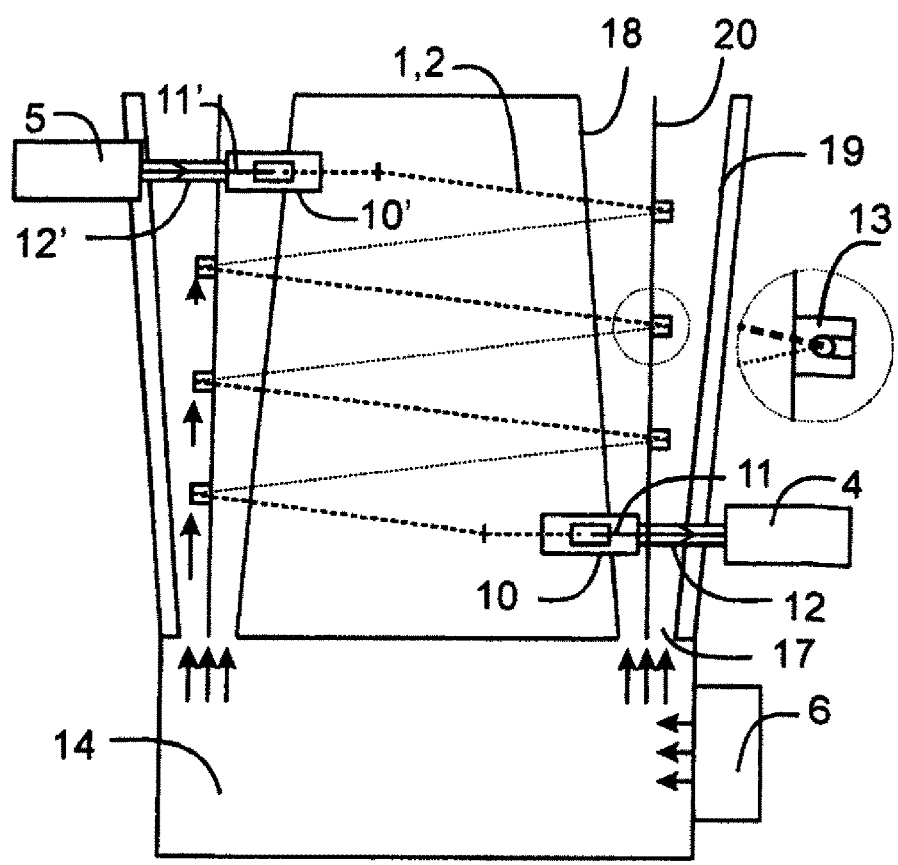
FIG. 4 shows a vertical section through a TGGC with a continuous increase in the flow cross section.

FIG. 4 shows a vertical section through a TGGC with a continuous increase in the flow cross section. In contrast to FIG. 3, the lateral wall surfaces (18 and 19) are both impermeable and formed obliquely to the flow direction. Wall surface (18) is the wall of a conical part standing in the interior of the arrangement. Wall surface (19) is the inner wall of a larger conical part situated on the outside, which has a smaller circumference at the bottom than at the top. In addition to geometrically conical embodiment of the wall surfaces (18, 19), different geometries with nonlinear profile shapes are possible. In addition to the oblique wall surfaces (18 and 19), the TGGC in this embodiment has a support structure (20) for the separation capillary (1) and/or sheath capillary (2), which guides the separation capillary (1) and/or sheath capillary (2) in the central region of the conical the expanding flow channel. The support structure (20) can consist of thin rods with the holding plates (13) mounted thereon, which are arranged in the center of the flow channel. Owing to the expansion of the flow cross section, the speed of flow decreases in accordance with the law of continuity. The heated separation capillary arranged therein is therefore subject to a flow with a speed of flow that decreases continuously from the bottom up. The thermal balance equilibrium therefore leads to low temperatures at the bottom and to high temperatures at the top, which act in the form of a continuous gradient over the entire separation capillary.

Figure 5:
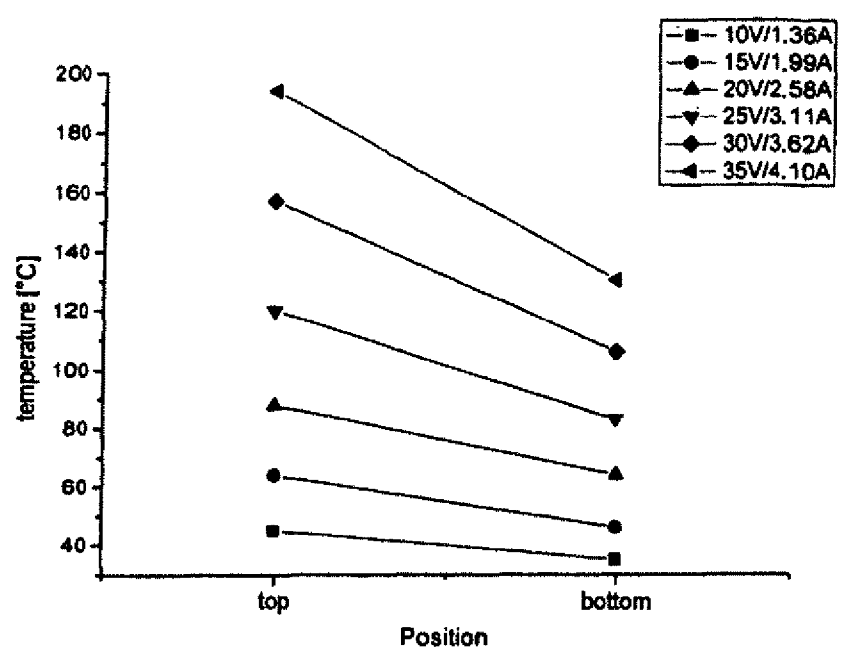
FIG. 5 shows a linear temperature profile of a TGGC without additional cooling media at different electric powers and with a constant flow field.

FIG. 5 shows a linear temperature profile of a TGGC without additional cooling media. The measurements indicate a linear temperature profile for the temperature variation in the separation capillary at different electric powers and with a constant flow field. There can also be deviations from the linear profile.

Figure 6:
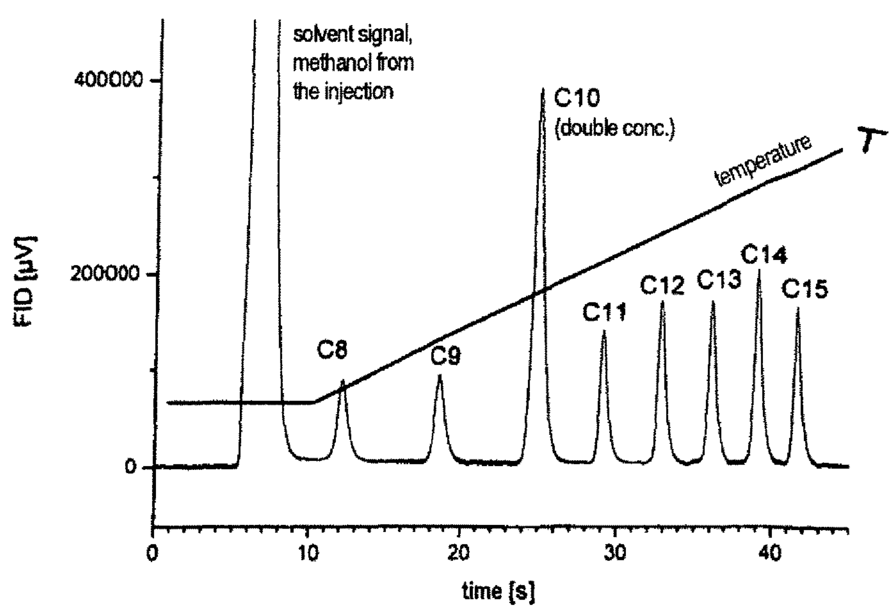
FIG. 6 shows the separation of substances in a mixture of C8 to C15 alkanes.

FIG. 6 shows the separation of substances in a mixture of C8 to C15 alkanes. During measurement, the temperature profile was raised quickly after injection. The focusing effect is evident particularly in the case of the longer-chain alkanes, which emerge at higher temperatures and therefore are subject to a somewhat steeper gradient and hence better focusing.

Figure 7:
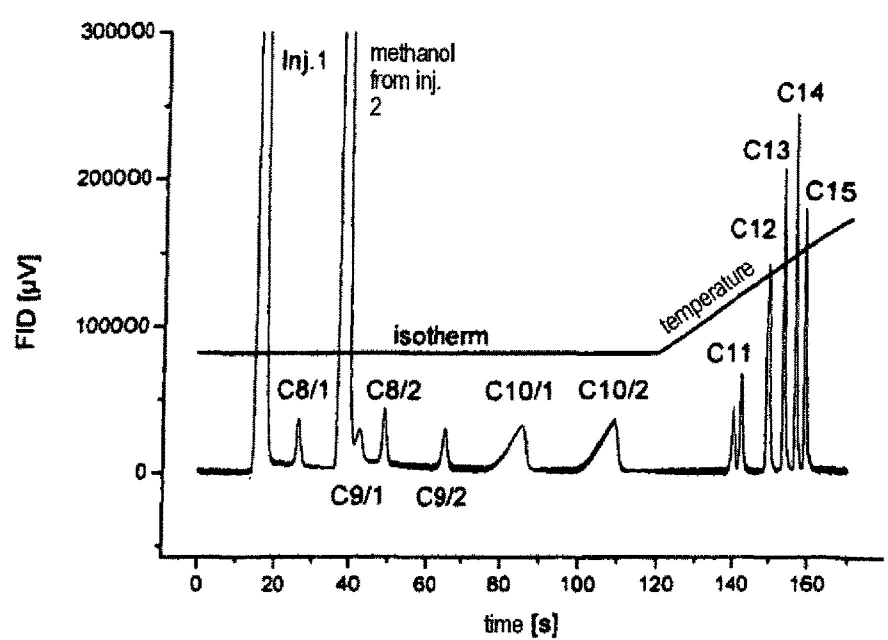
FIG. 7 demonstrates the enrichment effect with double injection of the mixture.

Finally, FIG. 7 demonstrates the enrichment effect with double injection of the mixture. An alkane mixture was injected at intervals of about 20 seconds. Normally, two series of signals then occur in succession. In the first part, the measurement was carried out at low temperature and here the occurrence of the double signals of the first and second injection is clearly apparent. The signal widths increase from C8 and C9 to C10 since the later components are already subject to longer running times with a higher diffusion. The less volatile substances from C11 upward collect on the separation column and do not emerge during the low temperatures of the isothermal phase. After the second signal of the C10 component, the temperature profile was raised quickly by raising the heating voltage. The following substances from C12 upward have already been focused at the same locations of the separation column and appear as narrow high signals. In gradient separations, the signal width is significantly reduced by the focusing effect.

LIST OF REFERENCE SIGNS

1 separation capillary
2 sheath capillary
3 groove
4 detector
5 sample feed
6 unit for producing a fluid flow
7 flow stabilizer
8 material
9 cover
10, 10' transfer ovens
11, 11' transfer lines
12, 12' auxiliary heating arrangements
13 holding plate
14 base
15 hollow cylinder
16 partially permeable wall surface
17 annular groove
18 wall surface (conical on the inside)
19 wall surface (conical on the outside)
20 support structure

The invention claimed is:

1. A device for gas-chromatic separation and determination of volatile substances in a carrier gas, having a resistance-heatable separation capillary (1) and/or a resistance-heatable sheath capillary (2) having a helical groove (3) distributed around the circumference, wherein porous material (8) is arranged within a hollow cylinder (15) in such a way that, by blowing in a fluid radially with respect to the separation capillary (1) and/or sheath capillary (2) from a unit for producing a fluid flow(6), a gradient of the flow speed is generated and a continuous temperature variation in the form of a gradient along the separation capillary (1) is produced.

2. The device as claimed in claim 1,
characterized in that the sheath capillary is surrounding the separation capillary (1) in the hollow cylinder (15).

3. The device as claimed in claim 1,
characterized in that the unit for producing a fluid flow (6) comprises a fan, a blower or a pressurized gas supply, and a temperature sensor.

4. The device as claimed in claim 1,
characterized in that the separation capillary (1) has a diameter in a range of from 0.3 mm
to 1 mm over a length of from 100 to 500 cm.

5. The device as claimed in claim 1,
characterized in that the sheath capillary (2) comprises a solid body.

* * * * *